United States Patent [19]

Ziegler

[11] Patent Number: 4,977,600
[45] Date of Patent: Dec. 11, 1990

[54] SOUND ATTENUATION SYSTEM FOR PERSONAL SEAT

[75] Inventor: Eldon W. Ziegler, Columbia, Md.

[73] Assignee: Noise Cancellation Technologies, Inc., Columbia, Md.

[21] Appl. No.: 203,114

[22] Filed: Jun. 7, 1988

[51] Int. Cl.⁵ ............................................. G10K 11/16
[52] U.S. Cl. ......................................... 381/71; 381/72
[58] Field of Search ............................... 381/71, 94, 72

[56] References Cited

U.S. PATENT DOCUMENTS

| | | |
|---|---|---|
| H417 | 1/1988 | Miles . |
| 2,972,018 | 2/1961 | Hawley et al. . |
| 2,983,790 | 5/1961 | Olson . |
| 4,061,875 | 12/1977 | Freifeld et al. . |
| 4,440,443 | 4/1984 | Nordskog . |
| 4,506,380 | 3/1985 | Matsui ................................. 381/71 |
| 4,562,589 | 12/1985 | Warnaka et al. . |
| 4,654,871 | 3/1987 | Chaplin et al. ..................... 381/94 |
| 4,683,590 | 7/1987 | Miyoshi et al. .................... 381/93 |
| 4,689,821 | 8/1987 | Salikuddin et al. . |

FOREIGN PATENT DOCUMENTS 2188210 9/1987 United Kingdom .

OTHER PUBLICATIONS

"Noise+Noise=Silence", Steve Cropley; *Autoweek,* Apr. 25, 1988, pp. 33,34.
John Free, "Noise Zapper", Popular Science, Jan., 1987, pp. 76,77,96.

*Primary Examiner*—Forester W. Isen
*Attorney, Agent, or Firm*—Birch, Stewart, Kolasch & Birch

[57] ABSTRACT

A sound cancellation system wherein a pair of sensors and actuators are positioned immediately adjacent an associated ear of an inhabitant of an enclosure so as to provide a cancellation zone immediately adjacent an associated ear without interfering with adjacent zones. A controller receives a synchronization signal so as to cancel a selected noise associated with a synchronization signal. The sensors and actuators are mounted to a seat which is to be occupied by an inhabitant of the enclosure.

16 Claims, 2 Drawing Sheets

SOUND ATTENUATION SYSTEM FOR PERSONAL SEAT

BACKGROUND AND SUMMARY OF THE INVENTION

The present invention relates generally to sound attenuators and more specifically to a sound attenuator for an enclosure.

Sound attenuators in the prior art have included passive as well as active attenuators. The use of sound absorbing material is a well-known passive attenuating technique. Active sound attenuators have taken two general approaches. The first is to attenuate the sound at its source. This generally includes measuring the sound at its source and producing a cancelling sound 180° out of phase at the source of the sound or noise. The second method is to cancel or attenuate the noise at a location, remote from the source of the noise, at which inhabitants are expected to occupy.

Within the second group of active sound attenuators in which the noise is cancelled or attenuated at a remote point from the source of the noise, two general overall methodologies have been developed. In the first methodology, noise is attenuated throughout the total enclosure. This generally would include measuring the noise level within the enclosure and providing appropriate cancelling noise to cancel the noise throughout the total enclosure. The less sophisticated systems use a few actuators to produce the cancelling noise where others do a complete study of the total enclosure finding the nodal points of maximum noise and placing the actuators at the maximum nodal point. This second system requires a substantial amount of time and research to determine the nodal points. This method and the less sophisticated systems depend on noise produced during a test period. The noise itself may have different nodal points or be noise different from that designed around and therefore, the anti-noise or cancelling signal produced by the actuators may not be effective. Also, the cancelling noise may combine with the noise level instead of cancelling and reducing it.

In addition to the dynamics of the enclosure, the interaction of the actuators must also be taken into account. This is especially true where the actuators are substantially displaced from the sensors and the actuator must be driven at sufficiently high amplitude. This substantially increases the complexity of the noise patterns within the enclosure.

A second methodology of cancelling the noise in an enclosure specifically at the location of the occupant or inhabitant includes placing earphones on the occupant. The earphones not only operate as a passive device for cancelling sound, they may also have actuators and sensors which measure and actively cancel the noise at the ears. These have generally been suggested for use in industrial environments where there are high levels of noise due to machinery or where a headset is naturally worn, for example by pilots.

In vehicles, which comprise an enclosure, or other space, it is highly desirable to cancel noise existing near the occupants produced by known sources of noise, for example, an engine or other periodically occurring noises of the vehicle, without adversely affecting the hearing of the driver/occupant. It is illegal in some states to wear earphones or other devices while driving since it is believed that it impairs the driver and other occupants from hearing emergency vehicles or being aware of other dangerous conditions about them. Thus, cancellation of the noise in the total enclosure has been the general approach to noise attenuation within the interior of the vehicle.

Thus it is an object of the present invention to provide a sound attenuation system which is localized with respect to the inhabitants without the use of earphones. Another object of the present invention is to provide localized attenuation of sounds in specific sub-zones of an enclosure without interaction of other sounds within the enclosure.

A still further object of the present invention is to provide an inexpensive sound attenuation system and method to provide localized sound attenuation for the inhabitants of an enclosed space at their positions of occupancy.

These and other objects are attained by mounting an acoustic sensor and actuator, at one or more selected locations of an enclosure, spaced from but immediately adjacent an occupant's ears at the selected location or locations. A synchronization signal is determined for the source of noise and used by a controller in combination with the sensed sounds from the sensor to control the actuator to cancel sounds from the noise source in a zone limited to the inhabitant at the specific selected location without adversely affecting other locations in the enclosure. Preferably, a pair of acoustic sensors and actuators are positioned immediately adjacent each ear of the inhabitant. The controller independently controls the actuators using the synchronization signal and the signal from the associated sensor to cancel the sound from the source of sound in the zone limited to the associated ear. The actuator and sensor should be sufficiently close to the ear to produce a localized zone and prevent interference between the actuators and sensors at each ear of an individual occupant as well as among the various occupants and zones. The sensor should be adjustable so as to be positioned as close as possible to the ear or ears of the occupant to maximize the accuracy of the measurement portion of the system. For the occupant of the vehicle, the sensor and actuator could be mounted to the seat to be occupied by the inhabitant.

Other objects, advantages and novel features of the present invention will become apparent from the following detailed description of the invention when considered in conjunction with the accompanying drawings.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE INVENTION

Figure 1:
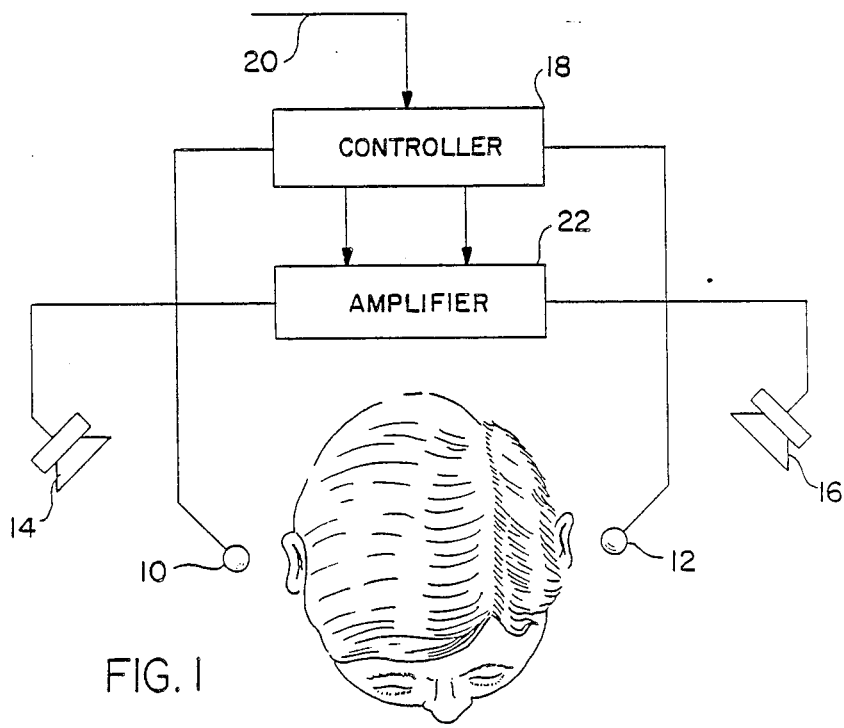
FIG. 1 is a schematic view of a noise cancellation system incorporating the principles of the present invention.

A noise cancellation system monitors the sound as close as possible to the inhabitant of an enclosed space, at its expected position, and provides a cancelling noise immediately adjacent the monitored area in such a manner as to not interfere with other zones or spaces throughout the enclosure. As illustrated in FIG. 1, microphones 10 and 12 are placed adjacent respective ears of an occupant and provide sensed input signals to a noise cancellation controller 18. The output of the noise cancellation controller is provided through amplifier 22 to a pair of actuators 14 and 16 which are adjacent associated sensors 10 and 12 and an associated ear of the occupant. A synchronized input signal 20 is also provided to the noise cancellation controller 18 so as to identify and cancel the synchronous noise. This allows cancellation of an identified noise signal while allowing other sounds to reach the ear of the inhabitant.

The controller 18 can be an NCT-2000, available from Noise Cancellation Technologies, Inc., of Columbia, Maryland. This would use a frequency domain technique as described in U.S. Pat. No. 4,490,841 to Chaplin et al. The singular controller can monitor and selectively control the appropriate zone adjacent each ear. Alternatively, a time domain technique may be used in controller 18. The technique used by the controller is not as important as the ability to monitor sound in a small zone and produce a cancelling sound in that zone so as not to interfere with adjacent zones.

The size of the zone of cancellation depends, in part, on the frequency to be cancelled and the complexity of the sound field. In complex sound fields found in small, enclosed, reverberant compartments, the zone of cancellation is formed from spheres centered on each sensor with a radius of approximately 1/10 of the wavelength of the frequency being cancelled. Thus, for example, in air a zone nearly two feet in radius is produced when cancelling a 60 Hz frequency while a zone of seven inches in radius is produced when cancelling a 200 Hz frequency.

Because of the size of the zones of cancellation, the preferred embodiment utilizes two sensors, one near each location which an inhabitant's ear will be during use.

The farther away the actuators 14 are from the area to be cancelled, the higher the sound level required at each actuator due to attenuation between the actuator and sensor. This increases the interaction between the actuator and the other sensors and therefore creates a more complicated problem as well as increasing sound levels at nearby locations. This will create nodes of cancellation as well as nodes of substantially increased levels.

The synchronization signal on line 20 may be from known sources of noise which are to be cancelled. Such noise may be from an engine in an automobile, or other well-known sources of reccurring noise or vibrations such as alternators or fans.

Figure 2:
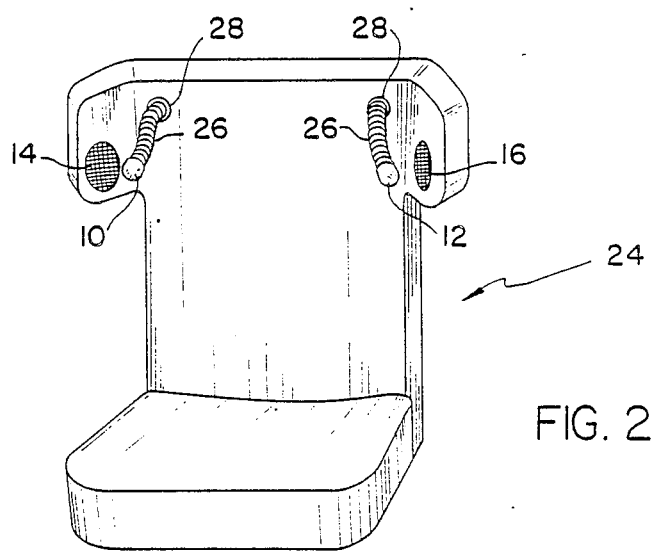
FIG. 2 is a perspective view of a system incorporating the principles of the present invention into a seat of a vehicle.

The application of the system of FIG. 1 to a vehicle seat is illustrated in FIG. 2. The vehicle seat 24 includes the sensors 12 and 14 mounted on flexible telescoping elements 26 which are pivotally mounted at locations 28 to the seat. This would be equivalent to an antenna construction. The actuators 14 and 16 are mounted in a wrap-around wing of the seat. The structure 26, 28 of the sensor mountings 10, 12 allow adjustment of the sensors 10, 12 to be placed immediately adjacent the ears of the inhabitant of the seat 24. The telescoping flexible section 26 as well as the pivotal mount 28 allows not only adjustment, but movement and deflection, in case movement of the head of the inhabitant causes contact with the sensors 10 and 12 and therefore no injury will result.

Placing the sensors 10 and 12 as close as possible to the ear of the inhabitant, the most accurate measurement of the noise adjacent the ear is measured. The actuators 14 and 16 are within a foot of the ear of the inhabitant and therefore, their zone of cancellation can be sufficiently small. They are also sufficiently separated from each other zone so as to not interfere with each other zone. Also, the amplitude of the signals produced by the actuators 14, 16 may be reduced since they are sufficiently close and the zone of cancellation is sufficiently small. By using low level signals from the actuators, the attenuation with distance is sufficiently great that at any zone of interaction, the interaction is minimal.

Figure 3:
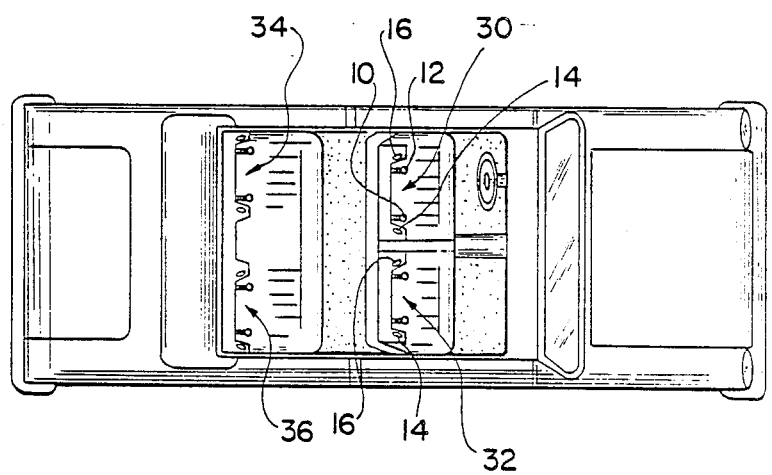
FIG. 3 is a perspective view of the incorporation of the principles of the present invention into a four-occupant vehicle.

As illustrated in FIG. 3, the front seat of a vehicle may include two cancellation systems 30 and 32 having individual noise cancellation systems, while the back seat includes individual cancellation systems 34, 36. Each noise cancellation system includes two pair of sensors and actuators, one adjacent each ear of the inhabitant of the seat. Although being illustrated for a automobile, the present system may be used in the enclosure of any vehicle, for example, trucks, construction equipment or farm equipment, as well as trains, planes and other types of vehicles. Similarly, a system of this type could be used in any other confined space where an inhabitant could be specifically located so that the sensor and actuator can be positioned as close as possible to the individual ears of the inhabitant such that a low amplitude noise cancellation signal can be applied to minimize and substantially eliminate any interference between the actuators and sensors of adjacent zones.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. An active noise attenuation system for attenuating selected noise at selected areas about an individual comprising:
   synchronization means for producing a synchronization signal for a source of noise to be attenuated;
   first and second acoustic actuators respectively mounted proximate each ear of the individual;
   first and second acoustic sensors respectively mounted between a corresponding one of said first and second acoustic actuators and a respective ear of the individual to be adjustably positionable in a lateral direction between said first and second acoustic actuators and the respective ear of the individual to accurately sense the sound adjacent the respective ear; and
   control means for independently controlling said first and second acoustic actuators using said synchronization signal and sounds sensed by the respective said first and second acoustic sensors to cancel the noise from said source of noise in a selected area limited to the individual without adversely affecting other locations in the vicinity.

2. The active noise attenuation system of claim 1 wherein said individual is positioned in a seat, said first and second acoustic actuators are mounted in respective first and second wrap-around wings of said seat proximate the respective ear, and said first and second acoustic sensors are respectively mounted via first and second adjustable supports on said seat.

3. The active noise attenuation system of claim 2 wherein said seat is positioned within an enclosure.

4. The active noise attenuation system of claim 3 wherein said enclosure includes a plurality of individuals positioned in respective seats and which cancels noise from said noise source in respective selected areas limited to each of said plurality of individuals.

5. The active noise attenuation system of claim 4 wherein said enclosure is that of a vehicle.

6. A method of active noise attenuation of selected noise at selected areas about an individual comprising the steps of:
producing a synchronization signal for a source of noise to be attenuated;
mounting respective first and second acoustic actuators proximate each ear of the individual;
sensing the sound adjacent each respective ear with first and second acoustic sensors mounted between a corresponding one of said first and second acoustic actuators and the respective ear of the individual to be adjustably positionable in a lateral direction between said first and second acoustic actuators and the respective ear of the individual; and
independently controlling said first and second acoustic actuators using said synchronization signal and sounds sensed by the respective said first and second acoustic sensors to cancel the noise from said source of noise in an area limited to the individual without adversely affecting other locations in the vicinity.

7. The method of active noise attenuation of claim 6 further comprising positioning said individual in a seat, mounting said first and second acoustic actuators in respective first and second wrap-around wings of said seat proximate the respective ear, and respectively mounting said first and second acoustic sensors via first and second adjustable supports on said seat.

8. The method of active noise attenuation of claim 7 further comprising positioning said seat within an enclosure.

9. The method of active noise attenuation of claim 8 further comprising positioning a plurality of individuals in respective seats and cancelling noise from said noise source in respective selected areas limited to each of said plurality of individuals.

10. The method of active noise attenuation of claim 9 wherein said enclosure is that of a vehicle.

11. An active noise attenuation seat for attenuating selected noise in respective first and second zones corresponding to each ear of a user comprising:
synchronization means for producing a synchronization signal for a source of noise to be attenuated;
first and second acoustic actuators, mounted in respective first and second wrap-around wings of the active sound attenuation seat to be located proximate a respective ear of the user;
first and second acoustic sensors, mounted on respective first and second adjustable supports to the active sound attenuation seat to be adjustably positionable in a lateral direction between the respective said first and second actuators and the respective ear of the user to accurately sense the sound in the respective first and second zones; and
control means for independently controlling said first and second acoustic actuators using said synchronization signal and sounds sensed by the respective said first and second acoustic sensors to cancel the noise from said source of noise in the respective first and second zones without adversely affecting other locations in the vicinity.

12. An active noise attenuation seat comprising:
synchronization means for producing a synchronization signal for a source of noise to be attenuated;
first and second wrap around wings extending from the seat to be proximate a respective ear of a user;
first and second acoustic actuators mounted in a corresponding one of said first and second wrap around wings;
first and second adjustable supports mounted to and extending from the seat, each of said adjustable supports including respective first and second ends, said first end mounted on the seat with said second end laterally positionable between a corresponding one of said first and second acoustic actuators and a respective ear of the user;
first and second acoustic sensors, mounted on a respective one of said second ends of said adjustable supports to accurately sense the sound in first and second zones corresponding to a respective ear of the user; and
control means for independently controlling said first and second acoustic actuators using said synchronization signal and sounds sensed by the respective said first and second acoustic sensors to cancel noise from said source of noise in each of said first and second zones without adversely affecting other locations in the vicinity.

13. An active noise attenuation seat comprising:
synchronization means for producing a synchronization signal for a source of noise to be attenuated;
first and second acoustic actuators respectively mounted on the seat proximate each ear of a user;
first and second adjustable supports mounted to the seat;
first and second acoustic sensors respectively mounted on a corresponding one of said first and second adjustable supports to be adjustable between a corresponding one of said first and second acoustic actuators and a respective ear of said user to accurately sense the sound adjacent the respective ear; and
control means for independently controlling said first and second acoustic actuators using said synchronization signal and sounds sensed by the respective said first and second acoustic sensors to cancel noise from said source of noise in a selected area limited to said user without adversely affecting other locations in the vicinity.

14. The active noise attenuation seat of claim 13 wherein said first and second acoustic actuators are mounted in respective first and second wrap-around wings of the seat proximate the respective ear.

15. The active noise attenuation seat of claim 14 wherein said seat is positioned within an enclosure.

16. The active noise attenuation seat of claim 15 wherein said enclosure is that of a vehicle.

* * * * *